United States Patent [19]

Suarato et al.

[11] 4,345,070
[45] Aug. 17, 1982

[54] PROCESS FOR THE PREPARATION OF 4'-DEOXY-DAUNORUBICIN AND 4'-DEOXY-DOXORUBICIN

[75] Inventors: Antonino Suarato; Sergio Penco, both of Milan; Federico Arcamone, Nerviano, all of Italy

[73] Assignee: Farmitalia Carlo Erba S.p.A., Milan, Italy

[21] Appl. No.: 270,877

[22] Filed: Jun. 5, 1981

[30] Foreign Application Priority Data

Sep. 29, 1980 [GB] United Kingdom ................. 8031382

[51] Int. Cl.$^3$ ........................................... C07H 15/24
[52] U.S. Cl. .................................. 536/17 A; 424/180
[58] Field of Search ................................ 536/17 A, 10

[56] References Cited

U.S. PATENT DOCUMENTS 3,886,138  5/1975  Naito et al. ............................ 536/10
4,067,969  1/1978  Penco et al. ....................... 536/17 A
4,112,076  9/1978  Arcamone et al. ................ 536/17 A
4,156,078  5/1979  Umezawa et al. ..................... 536/10

Primary Examiner—Johnnie R. Brown
Attorney, Agent, or Firm—Oblon, Fisher, Spivak, McClelland & Maier

[57] ABSTRACT

A new process for the preparation of the known 4'-deoxydaunorubicin and 4'-deoxydoxorubicin is disclosed. The used starting material is 4'-eip-N-trifluoroacetyldaunorubicin which is converted into 4'-deoxy-4'-iodo-N-trifluoroacetyl-daunorubicin from which 4'-deoxy-daunorubicin can be reductively obtained and eventually transformed, by known methods, into 4'-deoxy-doxorubicin.

3 Claims, No Drawings

PROCESS FOR THE PREPARATION OF 4'-DEOXY-DAUNORUBICIN AND 4'-DEOXY-DOXORUBICIN

The invention relates to a process for the preparation of 4'-deoxydaunorubicin and 4'-deoxydoxorubicin. These compounds are useful for the treatment of certain tumors in animals and have been described and claimed in U.S. Pat. No. 4,067,969. They have the formula

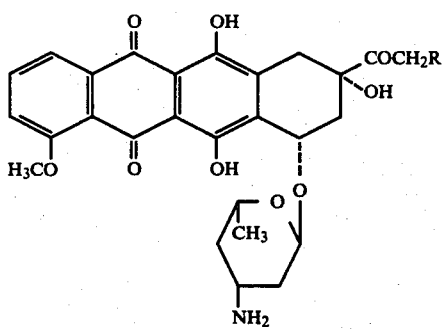

R representing a hydrogen atom in the case of 4'-deoxydaunorubicin and representing a hydroxy group in the case of 4'-deoxydoxorubicin.

The invention provides a process for the preparation of 4'-deoxydaunorubicin or 4'-deoxydoxorubicin, the process comprising replacing the C-4' hydroxy group of 4'-epi-N-trifluoroacetyldaunorubicin of the formula III with a halogen atom, reductively dehalogenating the resultant 4'-deoxy-4'-iodo-N-trifluoroacetyl-daunorubicin of the formula V, removing the N-protecting group from the resultant 4'-deoxy-N-trifluoroacetyl-daunorubicin of the formula VI to give 4'-deoxy-daunorubicin, and optionally converting the 4'-deoxy-daunorubicin to 4'-deoxy-doxorubicin by bromination and hydrolysis. A preferred embodiment of a process according to the invention is illustrated by the following reaction scheme:

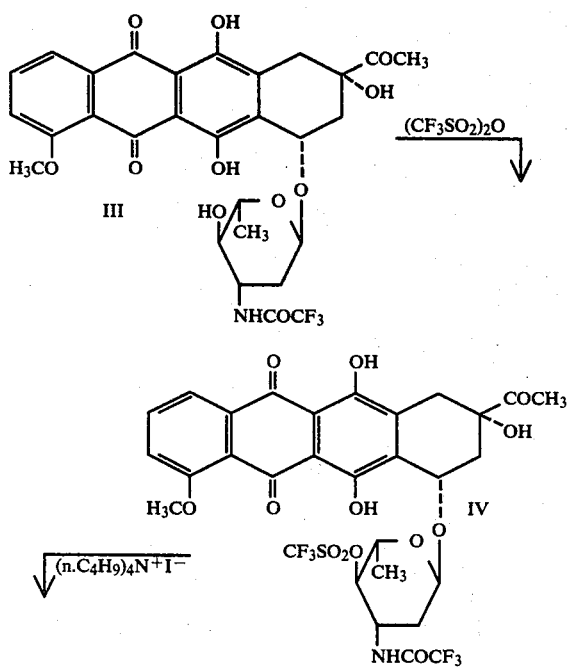

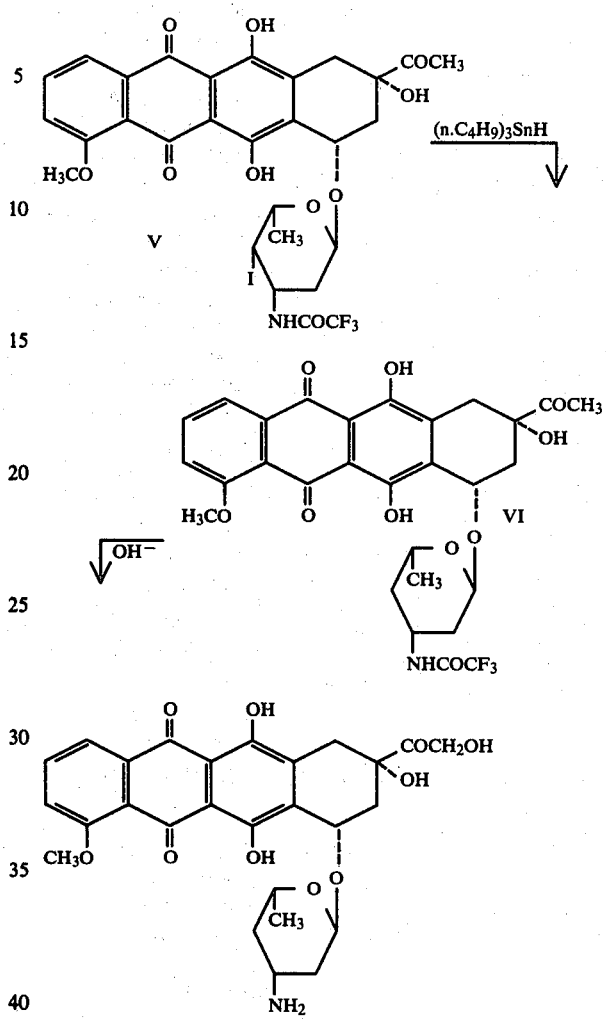

4'-deoxy-doxorubicin

In order to introduce a halogen atom at C-4' of III via an SN2 displacement reaction, the trifluoromethylsulphonyloxy group may be first introduced. The trifluoromethylsulphonyl derivative IV, which has not been previously described, allows the displacement to be carried out in mild conditions that do not affect the glycosidic linkage.

The reductive dehalogenation, suitably performed using tributyltin hydride in the presence of α,α'-azobis-(isobutyronitrile), is a radical-initiated reduction of a type not previously employed in anthracycline glycoside chemistry. Its use is essential in order to avoid the undesirable reductive splitting of the sugar moiety which readily occurs using other well-known reducing agents.

The starting material, 4'-epi-N-trifluoroacetyl-daunorubicin III, may be prepared as described in British Pat. No. 7940457. It should be stressed that only 4'-epi derivatives, such as III, having an equatorial hydroxyl group can give the trifluoromethylsulphonate. N-trifluoroacetyldaunorubicin, having an axial hydroxyl group, affords in the same conditions only degradation products. The introduction of the trifluoromethylsulphonyl group at C-4'-OH of III may be performed using trifluoromethylsulphonic anhydride in presence of pyridine at 0°. The formation of the ester can be monitored by thin layer chromatography, the disappearance of the starting material being complete in about 20 minutes.

The treatment of IV, dissolved in an organic solvent, such as methylene dichloride, with an excess of tetrabutylammonium iodide at 30° allows the isolation of the iododerivative V in high yield (75%) with almost complete preservation of the glycosidic linkage of IV, a feat not easily predictable. The reductive dehalogenation may be performed by treatment of V, dissolved in toluene, with two moles of tributyltin hydride in presence of α,α'-azobis (isobutyronitrile). The reaction is suitably carried out at refluxing temperature and the hydride added in four portions. The formation of 4'-deoxy-N-trifluoroacetyldaunorubicin VI can be monitored by thin layer chromathography: the disappearance of the starting material is complete in about 60 minutes.

Finally the N-protecting group may be removed by mild alkaline treatment. Subsequent treatment of the resultant 4'-deoxy-daunorubicin in accordance with the method described in U.S. Pat. No. 4,067,969 affords 4'-deoxy-doxorubicin.

The invention is illustrated by the following Examples.

EXAMPLE 1

4'-epi-4'-trifluoromethylsulphonyloxy-N-trifluoroacetyl-daunorubicin IV

To a stirred solution of 26 g of 4'-epi-N-trifluoroacetyldaunorubicin (III) in 650 ml of anhydrous methylene dichloride and 32 ml of anhydrous pyridine, cooled at 0° C., was added over a period of 20 minutes a solution of 11 ml of trifluoromethylsulphonic anhydride in 140 ml of anhydrous methylene dichloride. The organic phase was washed with a cooled 5% aqueous solution of sodium bicarbonate, water, a 0.1 N aqueous solution of hydrochloric acid and water in that order. The organic solution, dried over anhydrous sodium sulphate, was used in the following step without further purification.

TLC on Kieselgel plate F 254 (Merck) using chloroform: acetone (9:1 by volume) RF: 0.45.

EXAMPLE 2

4'-deoxy-4'-iodo-N-trifluoroacetyldaunorubicin V

To the solution in 1200 ml of methylene dichloride of 4'-epi-4'-trifluoromethylsulphonyloxy-N-trifluoroacetyldaunorubicin, obtained as described in Example 1, 23 g of tetrabutylammonium iodide were added. After 30 minutes at 30° C. the transformation was complete and the reaction mixture was washed with a 5% aqueous solution of sodium bicarbonate, water, a 0.1 N aqueous solution of hydrochloric acid and water in that order. Removal of the solvent by evaporation afforded V in crude form. This was purified by chromatography on a column of silica gel, eluting with methylenedichloride, to give 23 g of the title compound (yield 75%): FDMS [M+]: 733.

TLC on Kiesel gel plate F 254 (Merck) using chloroform: acetone (9:1 by volume) Rf: 0.54.

EXAMPLE 3

4'-deoxydaunorubicin, I (R=H)

A solution of 7.33 g of 4'-deoxy-4'-iodo-N-trifluoroacetyldaunorubicin V in 200 ml of anhydrous toluene at refluxing temperature was treated, under stirring and under a nitrogen atmosphere, with 7 ml of tributyltin hydride added in four portions over a period of 45 minutes and with 1 g of α,α'-azobis-isobutyronitrile. After 1 hour the reduction was complete then the reaction mixture was cooled at room temperature and poured into an excess of petroleum ether (40°-60° C.). The precipitate was collected by filtration, washed with petroleum ether and dried under vacuum. 4.55 g of 4'-deoxy-N-trifluoroacetyl-daunorubicin VI were obtained in 75% yield. The compound was dissolved in 300 ml of acetone and treated with 300 ml of a 0.1 N aqueous solution of sodium hydroxide at 10° C. for 3 hours. Then to the solution was added 0.1 N aqueous hydrochloric acid to adjust the pH to 4.5 and the aglycones were eliminated by extractions with chloroform. Then the aqueous solution was adjusted to pH 8.6 and repeatedly extracted with chloroform. The combined extracts were dried over anhydrous sodium sulphate, concentrated to a small volume and acidified to pH 4.5 with 0.1 N methanolic hydrogen chloride to allow crystallization of the title compound as its hydrochloride, m.p. 160°-164° C., $[\alpha]_D + 296°$ (c=0.05, methanol).

EXAMPLE 4

4'-deoxyadriamycin; I (R=OH)

A solution of 4'-deoxy-daunomycin prepared as described in Example 3 in a mixture of methanol and dioxane was treated with bromine to form the 14-bromo-derivative. Treatment of the 14-bromo derivative with an aqueous solution of sodium formate at room temperature for 100 hours gave 4'-deoxy-adriamycin which was isolated as the hydrochloride; m.p. 163° (dec); $[\alpha]_D^{20} = +320°$ (c=0.05 CH$_3$OH). TLC on Merck Kieselgel HF buffered at pH 7 with phosphate M/15 using methylene chloride-methanol-water (10:2:02) v/v) solvent system Rf 0.13.

What we claim is:

1. A process for the synthesis of 4'-deoxydaunorubicin; comprising:
   (a) reacting 4'-epi-N-trifluoroacetyldaunorubicin dissolved in methylene dichloride containing anhydrous pyridine with trifluoromethylsulfonic anhydride, thereby obtaining 4'-epi-4'-trifluoromethylsulfonyloxy-N-trifluoroacetyldaunorubicin as an intermediate;
   (b) reacting said intermediate with tetrabutylammonium iodide thereby obtaining 4'-deoxy-4'-iodo-N-trifluoroacetyldaunorubicin; and
   (c) reductively dehalogenating said iodo daunorubicin derivative with tributyltin hydride in the presence of alpha, alpha'-azobisisobutyronitrile, thereby yielding said 4'-deoxydaunorubicin product.

2. A process for synthesizing 4'-deoxydoxorubicin, comprising:
   brominating the 4'-deoxydaunorubicin product obtained by the process of claim 1, and hydrolyzing the brominated product in an aqueous reaction medium.

3. 4'-Deoxy-4'-iodo-N-trifluoroacetyldaunorubicin.

* * * * *